United States Patent [19]

Shoesmith

[11] Plant 4,753

[45] Jul. 21, 1981

[54] CHRYSANTHEMUM NAMED HUSKEY

[75] Inventor: Leonard H. Shoesmith, Westfield-Woking, England

[73] Assignee: Pan-American Plant Company, West Chicago, Ill.

[21] Appl. No.: 170,092

[22] Filed: Jul. 18, 1980

[51] Int. Cl.[3] ..... A01H 5/00

[52] U.S. Cl. ..... Plt./78

[58] Field of Search ..... Plt./78, 77

*Primary Examiner*—Robert E. Bagwill

*Attorney, Agent, or Firm*—Chas. W. Rummler

[57] ABSTRACT

A new and distinct chrysanthemum variety intended for Fall garden use and having a medium response, with a profusion of very light yellow flowers having a yellow-green button (disc) borne on strong, upright stems. The flowers are persistent and gradually turn whiter as they age. The plant grows vigorously and provides a mound of color in the garden in the Fall. This plant also is adaptable for year-around four inch pot production with eight-week response under photoperiod control.

4 Drawing Figures

BACKGROUND OF THE NEW PLANT

This new chrysanthemum cultivar originated as a seedling of unknown parentage growing among breeding stock maintained at West Chicago, Ill., where I discovered this new plant. The very light yellow coloration of the daisy-like flowers of this plant which gradually became whiter in color as the flowers matured prompted me to select this plant for propagation and test, which was done under my direction at West Chicago, Ill. Asexual propagation of this new variety by means of cuttings through several successive generations has shown that its novel characteristics hold true from generation to generation and appear to be firmly fixed. Propagation of this new plant by cuttings for the commercial market is now being done at West Chicago, Ill., and at Cortez, Fla.

DESCRIPTION OF THE DRAWINGS

This new chrysanthemum cultivar is illustrated by the accompanying drawings, of which sheet 1 is a full color photographic rendition showing a plurality of garden plants in full bloom; sheet 2 is a photographic close-up view of flowers of the new plant which has been hand-painted to show the true colors of the blooms according to specifications; and sheets 3 and 4 are, respectively, prints of machine copies of front and backside views of typical leaves of this new variety.

DESCRIPTION OF THE NEW PLANT

The following is a detailed description of my new cultivar of chrysanthemum based upon observation of plants grown at West Chicago, Ill., made in the Fall of 1979, the color renditions being according to The R.H.S. Colour Chart published by The Royal Horticultural Society of London, England.

THE PLANT

Origin: Seedling.
Parentage: Unknown.
Classification:
- *Botanic.*—*Chrysanthemum morifolium.*
- *Commercial.*—Chrysanthemum for garden culture adaptable for greenhouse pot culture.

Form: Bush of round shape.

Height: 50 to 75 cm.
Growth: Strong, vigorous and upright.
Growth rate: Rapid.
Branching character: Caespitose.
Foliage:
- *Quantity.*—Abundant.
- *Size of leaf.*—About 35 to 90 mm. long and 17 to 60 mm. wide.
- *Shape of leaf.*—Ovate with cleft margins.
- *Aspect.*—Canescent.
- *Venation.*—Pinnate.
- *Color.*—Upper side — 147A. Under side — 147B.
- *Petioles.*—Length: About 8 to 10 mm.

THE BUD

Form: Globular.
Size: Variable in both diameter and length.
Opening rate: Normal.
Color of florets:
- *When phyllaries first divide.*—145A.
- *When petals begin to unfurl.*—150B.

Phyllaries:
- *Number.*—Approximately 14.
- *Shape.*—Lanceolate.
- *Color.*—138D.

Peduncle:
- *Character.*—Rigid and erect.
- *Length.*—Variable.
- *Surface aspect.*—Canescent.
- *Color.*—138D.

THE FLOWER

Blooming habit: Profusely and intermittently.
Response: Mid-season of Fall in the garden and about eight weeks under photoperiod control for greenhouse pot production.
Natural flowering season: Mid-Fall.
Blooms:
- *Flower type.*—Daisy.
- *Size.*—Medium. Diameter — About 30 to 50 mm. Depth — About 10 to 15 mm.
- *Borne.*—Cymose.
- *Shape.*—When bloom first opens — Cup-shaped. When bloom matures — Flat.

Petalage:
- *Phyllaries.*—Approximately 14 in number.

*Florets.*—Number: Numerous both as ray and disc florets. Arrangement: Imbricated. Form: Obovate with entire margins and acuminate apex. Texture: Soft. Appearance: Satiny. Color: Ray florets: Body — 2D. Base — 2B. Reverse side — 1D. Disc florets — 1A deepening gradually to 143A at center.

*Discoloration after full bloom.*—Turns whiter as flower ages.

*Persistence.*—Petals hang on and dry.

Peduncle:

*Character.*—Strong and upright.

*Length.*—Variable.

*Color.*—138D.

Fragrance: Typical chrysanthemum.

Lasting quality:

*On plant.*—Four weeks.

*As cut flower.*—Not recommended.

REPRODUCTIVE ORGANS

Stamens: Many, in syngenesious arrangement.

*Anthers.*—Size: Insignificant. Color: Yellow-Green.

*Filaments.*—Length: Insignificant. Color: Yellow-Green.

*Pollen.*—Color: Yellow.

*Pistils.*—Number: One for each floret. Styles: Length: Insignificant. Color: Yellow-Green. Stigmas: Color: Yellow-Green.

Ovaries: Inferior bicarpellate.

This chrysanthemum cultivar is a new and distinct variety particularly adapted for the Fall garden and having a medium response for such use. The profusion of yellow-green button flowers produced by this plant and borne on strong stems provides a mound of color for garden decoration in the Fall. The flowers are persistent and the very pale yellow color of the flowers gradually turns whiter as the flower ages. This variety is also adaptable for year-around four inch pot production under photoperiod control and with an eight week flowering response.

I claim:

1. A new and distinct cultivar of *Chrysanthemum morifolium,* substantially as herein shown and described, particularly suitable for Fall garden culture and having a vigorous growth habit and a profuse production of flowers borne on strong, upright stems; this variety also being adaptable for year-around four inch pot production under photoperiod control.

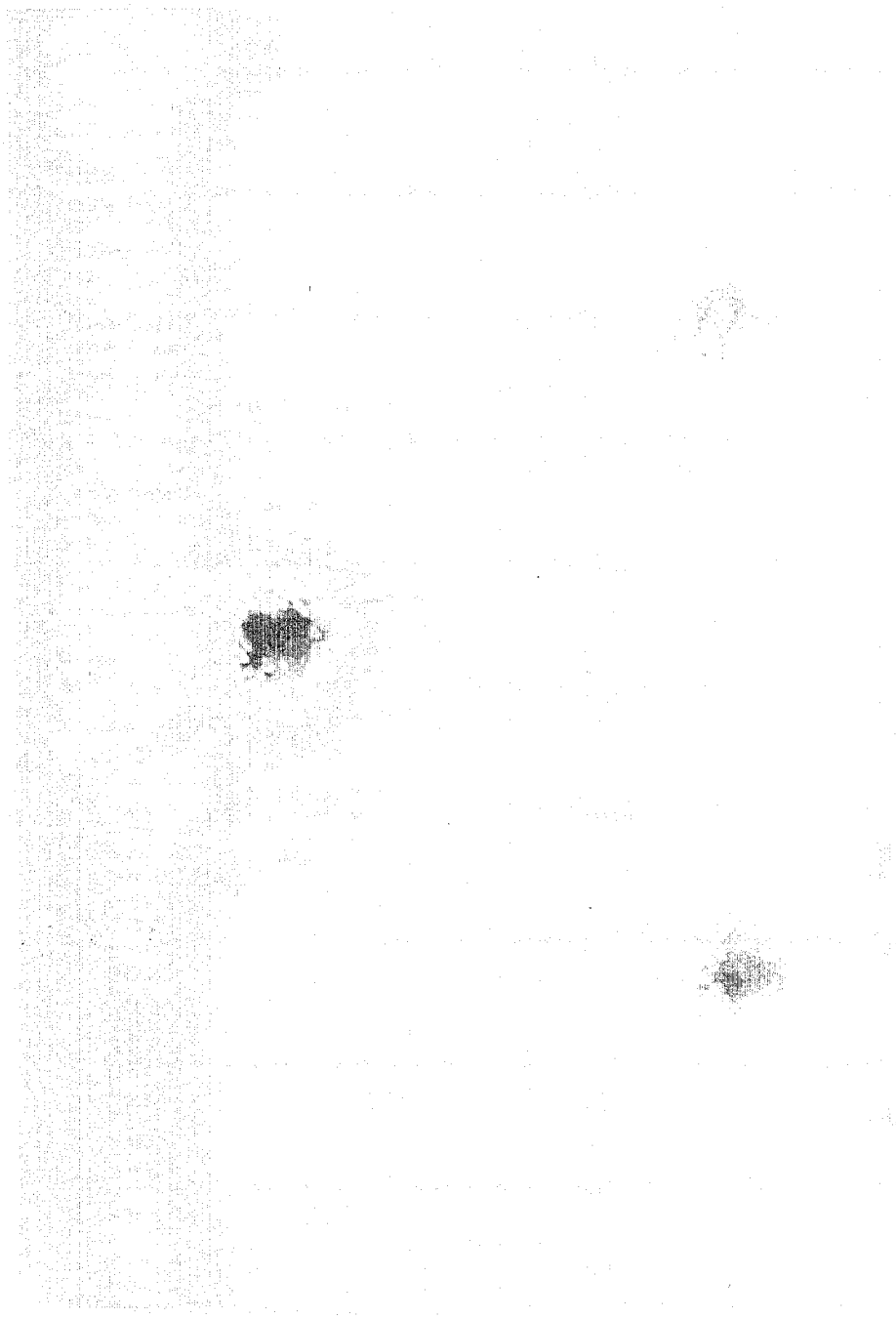

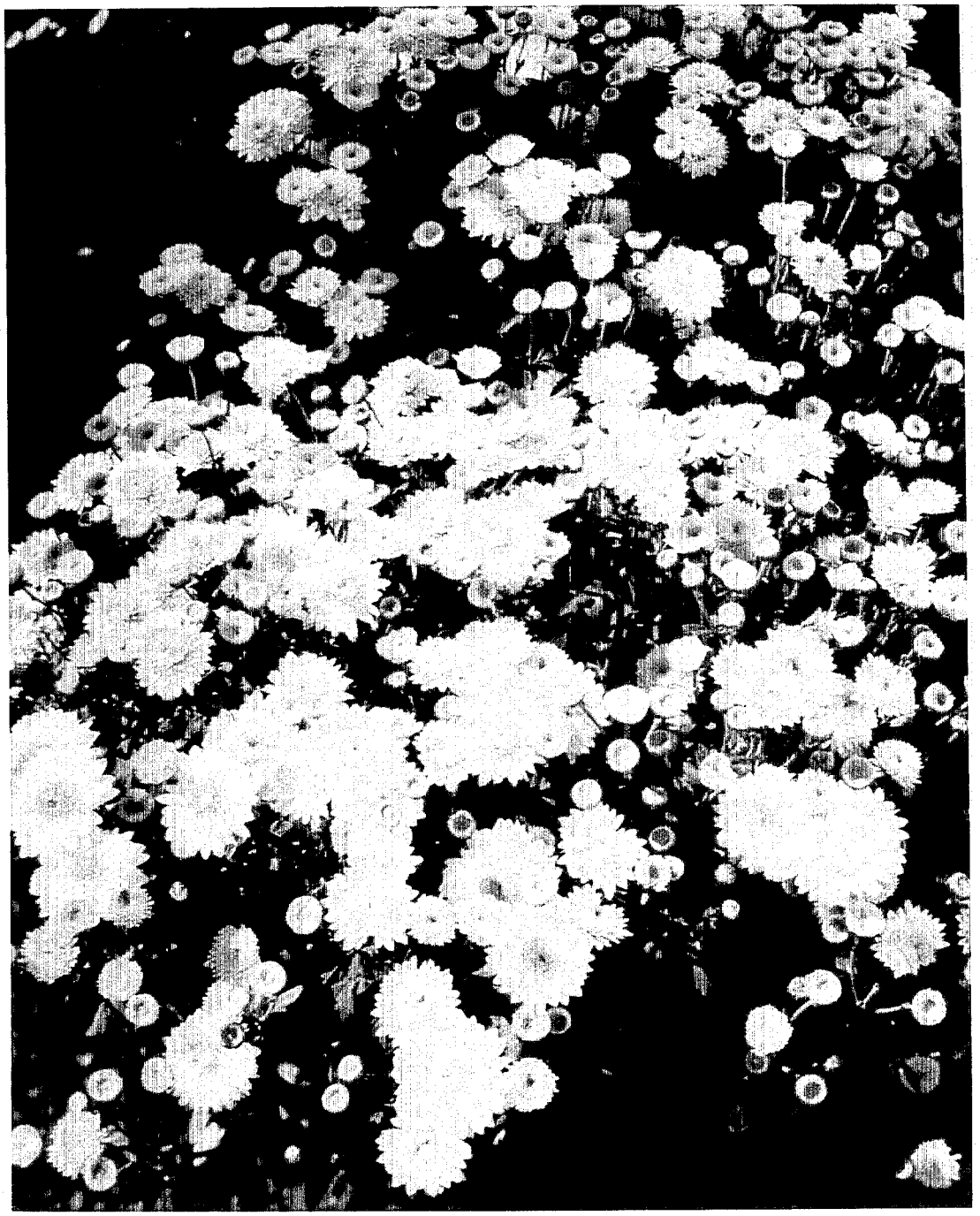

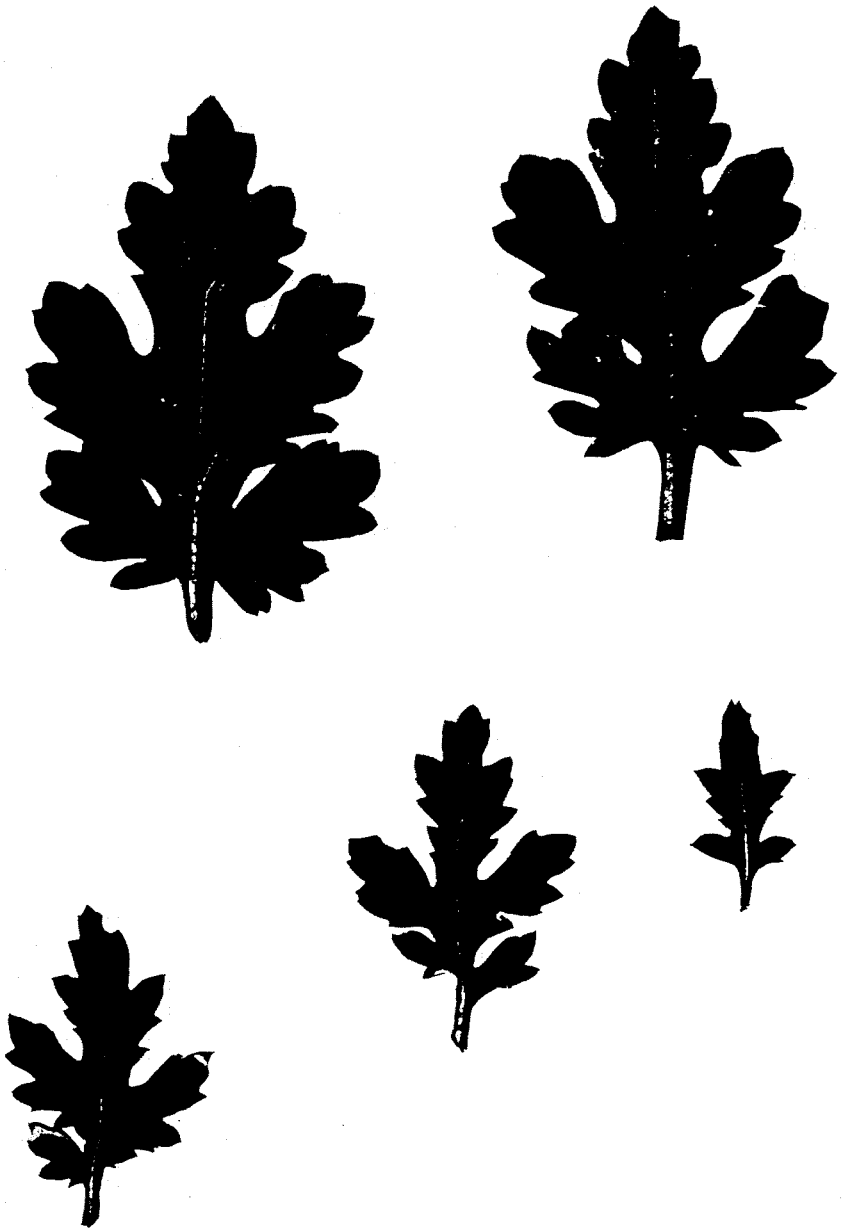

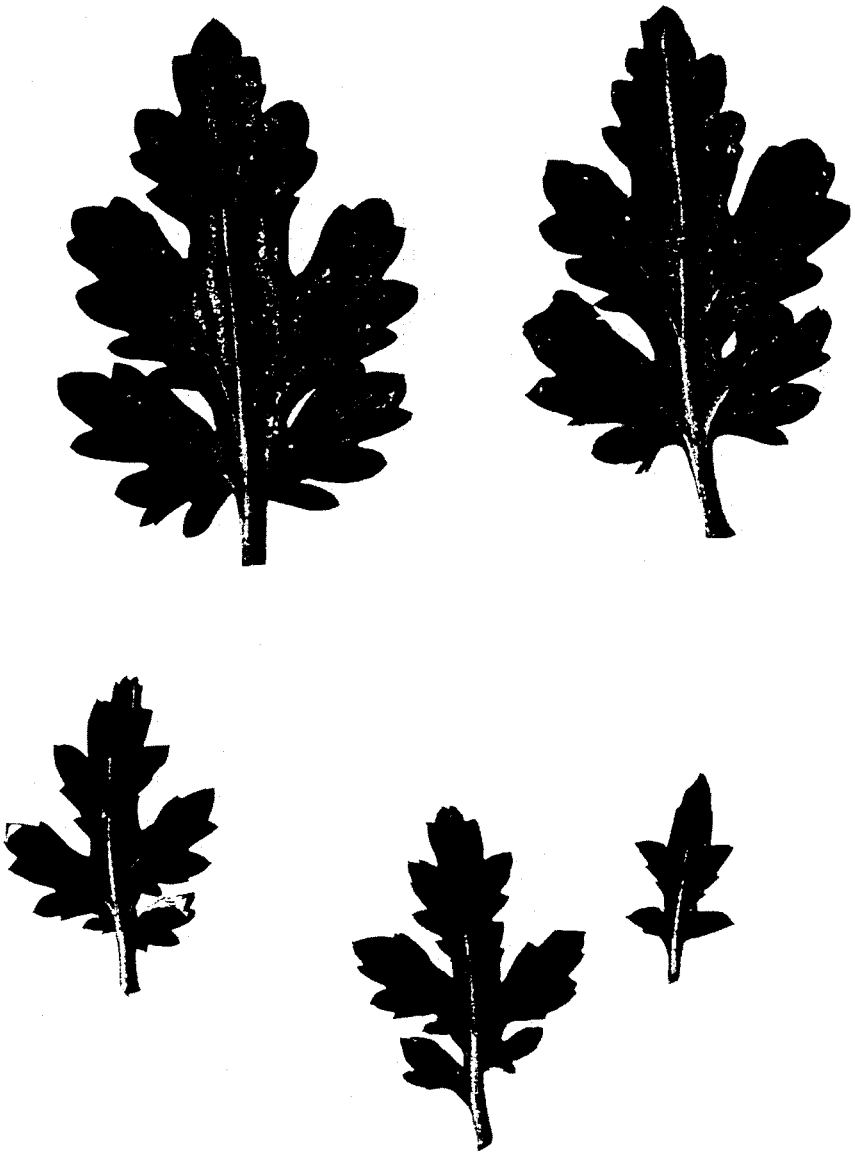

* * * * *